United States Patent (10) Patent No.: US 12,222,312 B2
Hagino et al. (45) Date of Patent: Feb. 11, 2025

(54) GAS SENSOR

(71) Applicant: DENSO CORPORATION, Kariya (JP)

(72) Inventors: Shota Hagino, Nisshin (JP); Satoshi Nakamura, Nisshin (JP); Masato Ozawa, Nisshin (JP)

(73) Assignee: DENSO CORPORATION, Kariya (JP)

( * ) Notice: Subject to any disclaimer, the term of this patent is extended or adjusted under 35 U.S.C. 154(b) by 569 days.

(21) Appl. No.: 17/526,610

(22) Filed: Nov. 15, 2021

(65) Prior Publication Data

US 2022/0074888 A1 Mar. 10, 2022

Related U.S. Application Data

(63) Continuation of application No. PCT/JP2020/016866, filed on Apr. 17, 2020.

(30) Foreign Application Priority Data

May 16, 2019 (JP) ................................. 2019-092852

(51) Int. Cl.
*G01N 27/407* (2006.01)
*G01N 33/00* (2006.01)
*G01N 27/409* (2006.01)

(52) U.S. Cl.
CPC ..... *G01N 27/4078* (2013.01); *G01N 33/0009* (2013.01); *G01N 27/409* (2013.01)

(58) Field of Classification Search
CPC .. G01N 27/403; G01N 27/406; G01N 27/407; G01N 27/4078; G01N 27/409; G01N 33/0009

See application file for complete search history.

(56) References Cited

U.S. PATENT DOCUMENTS 6,672,132 B1 1/2004 Weyl et al.

FOREIGN PATENT DOCUMENTS

| JP | 2-91955 | 7/1990 |
|----|---------|--------|
| JP | 9-318580 | 12/1997 |
| JP | 2001-133431 | 5/2001 |
| JP | 2001-311717 | 11/2001 |
| JP | 2012-154774 | 8/2012 |
| WO | 2019/088026 | 5/2019 |

OTHER PUBLICATIONS

English Machine Translation of JP2001133431 (Year: 2001).*

* cited by examiner

*Primary Examiner* — Gurpreet Kaur
(74) *Attorney, Agent, or Firm* — Nixon & Vanderhye P.C.

(57) ABSTRACT

A gas sensor includes a sensor element, a housing, a contact terminal, a second insulator, a lead wire, a sealing member, an inner periphery side cover and an outer periphery side cover. The inner periphery side cover is mounted on an outer periphery at a position on a base end side in an axial direction of the housing. The outer periphery side cover is disposed on the outer periphery side of the inner periphery side cover, forms a substantially cylindrical space with the inner periphery side cover and holds the sealing member on an inner periphery side.

4 Claims, 8 Drawing Sheets

GAS SENSOR

CROSS-REFERENCE TO RELATED APPLICATION

This application is the U.S. bypass application of International Application No. PCT/JP2020/016866 filed on Apr. 17, 2020 which designated the U.S. and claims priority to Japanese Patent Application No. 2019-092852 filed on May 16, 2019 the contents of both of which are incorporated herein by reference.

TECHNICAL FIELD

The present disclosure relates to a gas sensor including a sensor element.

BACKGROUND

For example, an in-vehicle gas sensor is disposed at an exhaust pipe of an internal combustion engine of a vehicle and is used to obtain an air-fuel ratio of the internal combustion engine based on a detection target gas, concentration of oxygen in the detection target gas, or the like, using an exhaust gas which flows through the exhaust pipe as the detection target gas. In the gas sensor, a sensor element including a detection unit is disposed within a cylindrical housing, the detection unit of the sensor element is covered with a distal end side cover mounted on the housing, and a wiring portion of the sensor element is covered with a base end side cover mounted on the housing. The detection unit of the sensor element and the distal end side cover are disposed inside the exhaust pipe, and the base end side cover is disposed outside the exhaust pipe.

SUMMARY

One aspect of the present disclosure is a gas sensor including a sensor element which includes a detection unit which is capable of detecting a gas at a position on a distal end side in an axial direction thereof,
a cylindrical housing in which the sensor element is disposed in a state where the detection unit projects on a distal end side in the axial direction,
a contact terminal which is in contact with a terminal portion provided at a position on a base end side in the axial direction of the sensor element,
an insulator holding the contact terminal,
a lead wire connected to the contact terminal and drawn outside,
a sealing member holding the lead wire,
an inner periphery side cover mounted on an outer periphery side of the housing at a position on the base end side in the axial direction, and
an outer periphery side cover disposed on an outer periphery side of the inner periphery side cover, forming a substantially cylindrical space with the inner periphery side cover, and holding the sealing member on an inner periphery side.
A distal end portion in the axial direction of the inner periphery side cover is mounted on an outer periphery of the housing at a position on the base end side in the axial direction by bonding, press fitting or swaging,
an end portion on the distal end side in the axial direction of the substantially cylindrical space is closed by an entire circumference of a distal end portion in the axial direction of the outer periphery side cover being mounted on an entire circumference of a distal end portion in the axial direction of the inner periphery side cover by bonding, press fitting or swaging,
the substantially cylindrical space is formed by an outer diameter of the inner periphery side cover being smaller at the distal end portion in the axial direction than at a portion located on the base end side of the distal end portion, and
an opening on the base end side in the axial direction of the substantially cylindrical space is open by a proximal portion in the axial direction of the inner periphery side cover being disposed on an inner periphery side of the outer periphery side cover.

Another aspect of the present disclosure is a gas sensor including a sensor element which includes a detection unit which is capable of detecting a gas at a position on a distal end side in an axial direction thereof,
a cylindrical housing in which the sensor element is disposed in a state where the detection unit projects on a distal end side in the axial direction,
a contact terminal which is in contact with a terminal portion provided at a position on a base end side in the axial direction of the sensor element,
an insulator holding the contact terminal,
a lead wire connected to the contact terminal and drawn outside,
a sealing member holding the lead wire,
an inner periphery side cover mounted on an outer periphery side of the housing at a position on the base end side in the axial direction, and
an outer periphery side cover disposed on an outer periphery side of the inner periphery side cover, forming a substantially cylindrical space with the inner periphery side cover, and holding the sealing member on an inner periphery side.
A distal end portion in the axial direction of the inner periphery side cover is mounted on an outer periphery of the housing at a position on the base end side in the axial direction by bonding, press fitting or swaging,
an end portion on the distal end side in the axial direction of the substantially cylindrical space is closed by a bent distal end portion formed by being bent on an inner periphery side in a radial direction at an entire circumference of a distal end portion in the axial direction of the outer periphery side cover being mounted on an entire circumference of a distal end portion in the axial direction of the inner periphery side cover by bonding, press fitting or swaging,
the substantially cylindrical space is formed by an interval being provided between the outer periphery side cover and the inner periphery side cover by the bent distal end portion, and
an opening on the base end side in the axial direction of the substantially cylindrical space is open by a proximal portion in the axial direction of the inner periphery side cover being disposed on an inner periphery side of the outer periphery side cover.

Yet another aspect of the present disclosure is a gas sensor including a sensor element which includes a detection unit which is capable of detecting a gas at a position on a distal end side in an axial direction thereof,
a cylindrical housing in which the sensor element is disposed in a state where the detection unit projects on a distal end side in the axial direction,
a contact terminal which is in contact with a terminal portion provided at a position on a base end side in the axial direction of the sensor element, an insulator holding the contact terminal,
a lead wire connected to the contact terminal and drawn outside,
a sealing member holding the lead wire,
an inner periphery side cover mounted on an outer periphery side of the housing at a position on the base end side in the axial direction, and
an outer periphery side cover disposed on an outer periphery side of the inner periphery side cover, forming a substantially cylindrical space with the inner periphery side cover, and holding the sealing member on an inner periphery side.

A second thickness of the inner periphery side cover is greater than a first thickness of the outer periphery side cover.

BRIEF DESCRIPTION OF THE DRAWINGS

The above features of the present disclosure will be made clearer by the following detailed description, given referring to the appended drawings. In the accompanying drawings.

DETAILED DESCRIPTION OF THE PREFERRED EMBODIMENTS

A temperature of an exhaust gas which passes through the exhaust pipe of the internal combustion engine becomes high, for example, approximately 1100° C. due to internal combustion of a fuel in the internal combustion engine. Then, heat is transferred from the exhaust pipe which is heated at a high temperature to the housing attached to the exhaust gas, and the heat is transferred from the housing to the base end side cover. Further, a rubber sealing member for holding a lead wire electrically connected to the sensor element is disposed on an inner periphery side of the base end side cover, and heat is also transferred from the base end side cover to the sealing member.

Examples of techniques for protecting a sealing member from heat can include, for example, a gas sensor disclosed in JP 2012-154774 A. At this gas sensor, a heat dissipation member which projects on an outer periphery side is attached to an external cylinder (base end side cover) attached on an outer periphery of a main metal fitting (housing) to prevent thermal degradation of a rubber cap (sealing member).

At a gas sensor in JP 2012-154774 A, after heat is transferred from a housing to a base end side cover, the heat is released from the base end side cover to a heat dissipation member. Thus, the heat transferred from the housing to the base end side cover is transferred through a path through which heat is released from the base end side cover to the heat dissipation member and a path through which heat is transferred from the base end side cover to the sealing member. As a result of this, it is difficult to sufficiently prevent heat from being transferred from the base end side cover to the sealing member at the gas sensor in JP 2012-154774 A.

The present disclosure is directed to providing a gas sensor which is capable of effectively protecting a sealing member from heat by making the sealing member less likely to be heated by heat transferred from a housing.

One aspect of the present disclosure is a gas sensor including a sensor element which includes a detection unit which is capable of detecting a gas at a position on a distal end side in an axial direction thereof,
a cylindrical housing in which the sensor element is disposed in a state where the detection unit projects on a distal end side in the axial direction,
a contact terminal which is in contact with a terminal portion provided at a position on a base end side in the axial direction of the sensor element,
an insulator holding the contact terminal,
a lead wire connected to the contact terminal and drawn outside,
a sealing member holding the lead wire,
an inner periphery side cover mounted on an outer periphery side of the housing at a position on the base end side in the axial direction, and
an outer periphery side cover disposed on an outer periphery side of the inner periphery side cover, forming a substantially cylindrical space with the inner periphery side cover, and holding the sealing member on an inner periphery side.

A distal end portion in the axial direction of the inner periphery side cover is mounted on an outer periphery of the housing at a position on the base end side in the axial direction by bonding, press fitting or swaging,
an end portion on the distal end side in the axial direction of the substantially cylindrical space is closed by an entire circumference of a distal end portion in the axial direction of the outer periphery side cover being mounted on an entire circumference of a distal end portion in the axial direction of the inner periphery side cover by bonding, press fitting or swaging,
the substantially cylindrical space is formed by an outer diameter of the inner periphery side cover being smaller at the distal end portion in the axial direction than at a portion located on the base end side of the distal end portion, and
an opening on the base end side in the axial direction of the substantially cylindrical space is open by a proximal portion in the axial direction of the inner periphery side cover being disposed on an inner periphery side of the outer periphery side cover.

Another aspect of the present disclosure is a gas sensor including a sensor element which includes a detection unit which is capable of detecting a gas at a position on a distal end side in an axial direction thereof,
a cylindrical housing in which the sensor element is disposed in a state where the detection unit projects on a distal end side in the axial direction,
a contact terminal which is in contact with a terminal portion provided at a position on a base end side in the axial direction of the sensor element, an insulator holding the contact terminal, a lead wire connected to the contact terminal and drawn outside, a sealing member holding the lead wire, an inner periphery side cover mounted on an outer periphery side of the housing at a position on the base end side in the axial direction, and an outer periphery side cover disposed on an outer periphery side of the inner periphery side cover, forming a substantially cylindrical space with the inner periphery side cover, and holding the sealing member on an inner periphery side.

A distal end portion in the axial direction of the inner periphery side cover is mounted on an outer periphery of the housing at a position on the base end side in the axial direction by bonding, press fitting or swaging, an end portion on the distal end side in the axial direction of the substantially cylindrical space is closed by a bent distal end portion formed by being bent on an inner periphery side in a radial direction at an entire circumference of a distal end portion in the axial direction of the outer periphery side cover being mounted on an entire circumference of a distal end portion in the axial direction of the inner periphery side cover by bonding, press fitting or swaging, the substantially cylindrical space is formed by an interval being provided between the outer periphery side cover and the inner periphery side cover by the bent distal end portion, and an opening on the base end side in the axial direction of the substantially cylindrical space is open by a proximal portion in the axial direction of the inner periphery side cover being disposed on an inner periphery side of the outer periphery side cover.

Yet another aspect of the present disclosure is a gas sensor including a sensor element which includes a detection unit which is capable of detecting a gas at a position on a distal end side in an axial direction thereof, a cylindrical housing in which the sensor element is disposed in a state where the detection unit projects on a distal end side in the axial direction, a contact terminal which is in contact with a terminal portion provided at a position on a base end side in the axial direction of the sensor element, an insulator holding the contact terminal, a lead wire connected to the contact terminal and drawn outside, a sealing member holding the lead wire, an inner periphery side cover mounted on an outer periphery side of the housing at a position on the base end side in the axial direction, and an outer periphery side cover disposed on an outer periphery side of the inner periphery side cover, forming a substantially cylindrical space with the inner periphery side cover, and holding the sealing member on an inner periphery side.

A second thickness of the inner periphery side cover is greater than a first thickness of the outer periphery side cover.

In the gas sensor according to the aspects, the base end side cover to be mounted on the outer periphery on the base end side in the axial direction of the housing is constituted with the inner periphery side cover and the outer periphery side cover which forms a substantially cylindrical space with the inner periphery side cover. Further, heat to be transferred from a portion at which the gas sensor is attached to the housing can be transferred from the housing to the inner periphery side cover.

As a result of the substantially cylindrical space being formed between the inner periphery side cover and the outer periphery side cover, heat to be transferred from the inner periphery side cover to the outer periphery side cover is minimized. Further, heat is less likely to be transferred from the housing to the outer periphery side cover, and heat is less likely to be transferred from the outer periphery side cover to the sealing member disposed on the inner periphery side of the outer periphery side cover.

Thus, according to the gas sensor according to the aspects, it is possible to effectively protect the sealing member from heat by making the sealing member less likely to be heated by heat transferred from the housing.

A preferred embodiment according to the gas sensor described above will be described with reference to the drawings.

EMBODIMENT

As illustrated in FIG. 1 to FIG. 4, a gas sensor 1 of the present embodiment includes a sensor element 2, a housing 41, contact terminals 44, a second insulator 43 as an insulator, lead wires 48, a sealing member 47, an inner periphery side cover 5 and outer periphery side covers 46A and 46B. The sensor element 2 includes a detection unit 21 which is capable of detecting a gas at a position on a distal end side L1 in an axial direction L. The housing 41 is formed in a cylindrical shape, and the sensor element 2 is inserted into an inner periphery side of the housing 41. The detection unit 21 of the sensor element 2 projects on the distal end side L1 from an end surface on the distal end side L1 in the axial direction L of the housing 41.

Figure 2:
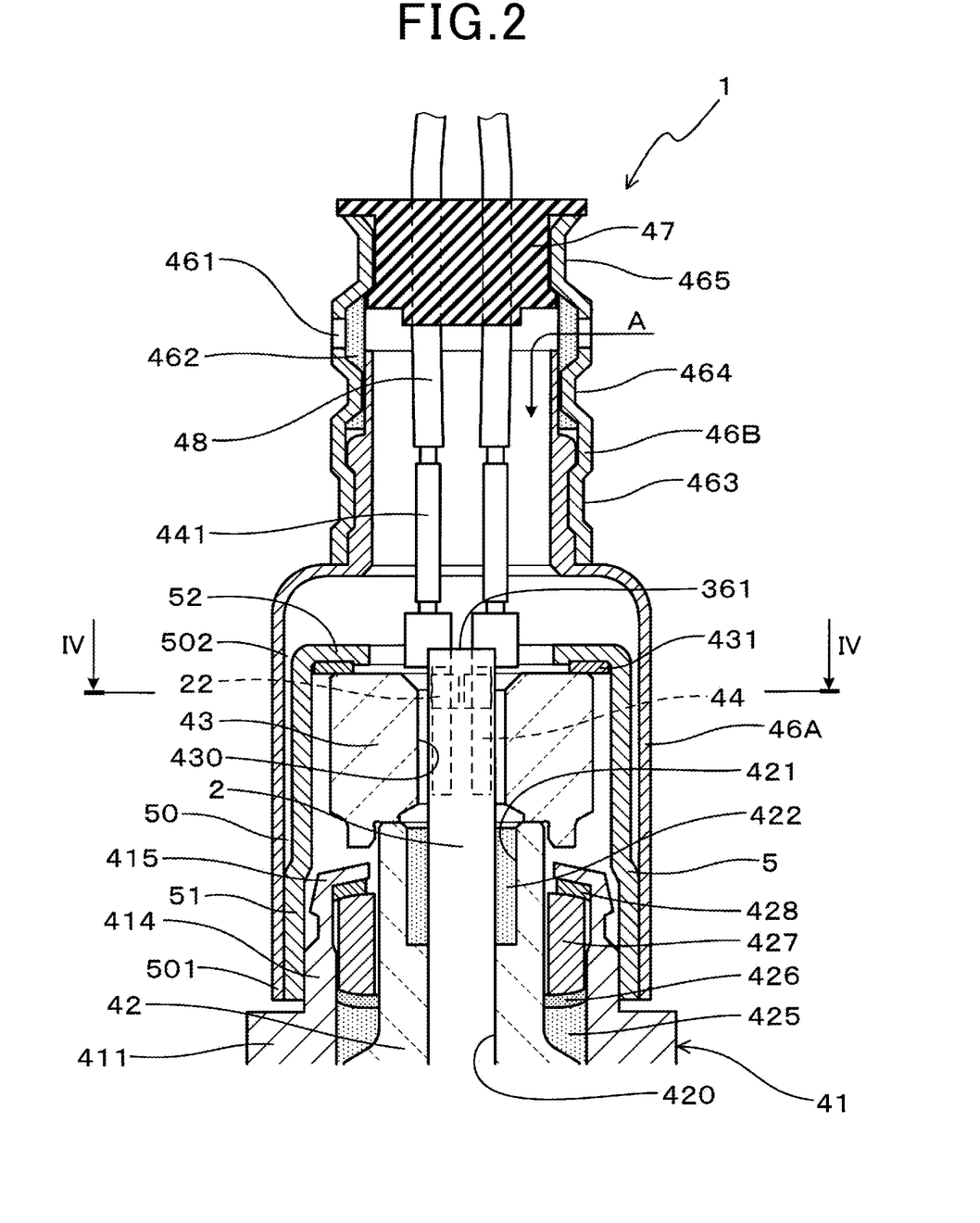
FIG. 2 is an explanatory diagram illustrating an enlarged cross-section of a proximal end portion in an axial direction of the gas sensor in FIG. 1.
Figure 4:
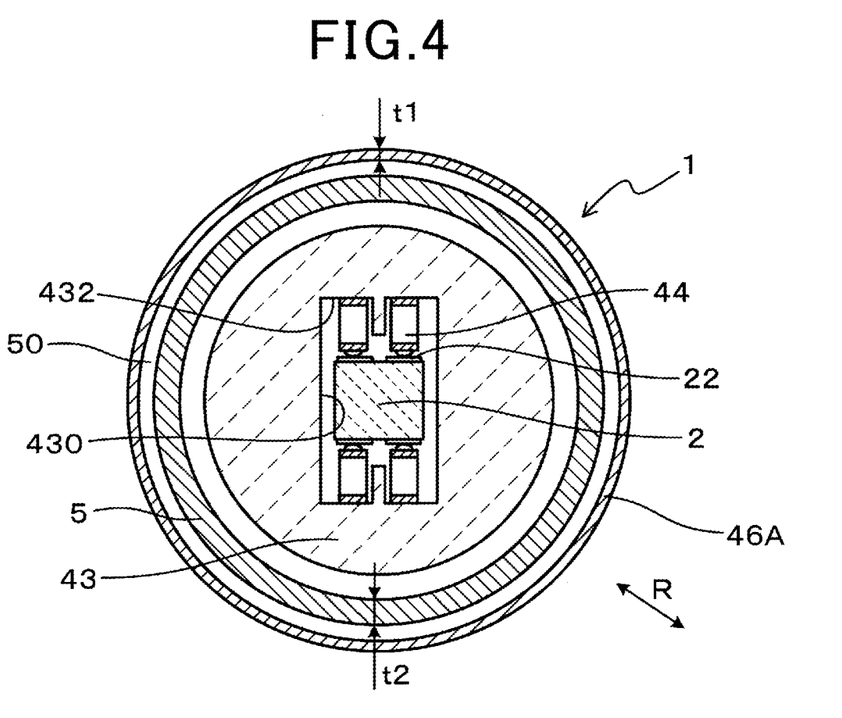
FIG. 4 is an explanatory diagram illustrating a cross-section IV-IV in FIG. 2.

As illustrated in FIG. 2 and FIG. 4, the contact terminals 44 are in contact with terminal portions 22 provided at positions on a base end side L2 in the axial direction L of the sensor element 2. The second insulator 43 holds the contact terminals 44. The lead wires 48 are connected to the contact terminals 44 and are drawn outside the gas sensor 1. The sealing member 47 holds the lead wires 48. The inner periphery side cover 5 is mounted on an outer periphery at the position on the base end side L2 in the axial direction L of the housing 41. The outer periphery side covers 46A and 46B are disposed on an outer periphery side of the inner periphery side cover 5, form a substantially cylindrical space 50 with the inner periphery side cover 5, and hold the sealing member 47 on the inner periphery side.

The gas sensor 1 according to the present embodiment will be described in detail below.

[Gas Sensor 1]

Figure 1:
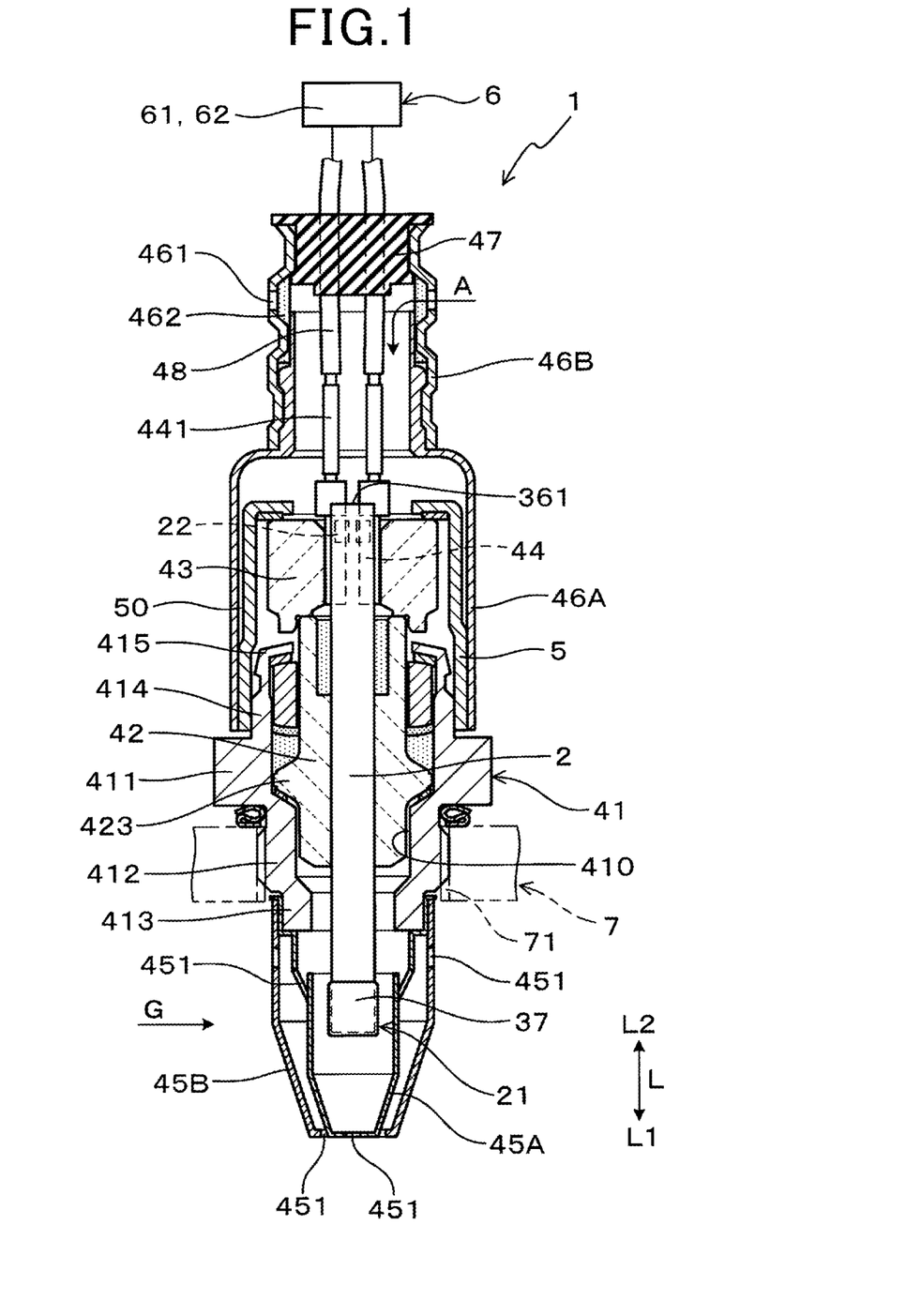
FIG. 1 is an explanatory diagram illustrating a cross-section of a gas sensor according to an embodiment.

As illustrated in FIG. 1, the gas sensor 1 is disposed at a mounting port 71 of an exhaust pipe 7 of an internal combustion engine of a vehicle, and is used to detect oxygen concentration, or the like, in a detection target gas using an exhaust gas G which flows through the exhaust pipe 7 as the detection target gas. The gas sensor 1 can be used as an air-fuel ratio sensor (A/F sensor) which obtains an air-fuel ratio in the internal combustion engine based on the oxygen concentration, unburnt gas concentration, or the like, in the exhaust gas G. The air-fuel ratio sensor can quantitatively and continuously detect an air-fuel ratio from a fuel rich state where a ratio of a fuel with respect to air is higher than a theoretical air-fuel ratio to a fuel lean state where the ratio of a fuel with respect to air is lower than the theoretical air-fuel ratio. The gas sensor 1 can be further used in various purposes for obtaining oxygen concentration other than the air-fuel ratio sensor.

A catalyst for purifying toxic substances in the exhaust gas G is disposed at the exhaust pipe 7, and the gas sensor 1 can be disposed at either on an upstream side or on a downstream side of the catalyst in a flow direction of the exhaust gas G at the exhaust pipe 7. Further, the gas sensor 1 can be also disposed at a pipe on an intake side of a supercharger which increases density of air to be supplied to the internal combustion engine by utilizing the exhaust gas G. Further, as the pipe at which the gas sensor 1 is to be disposed, a pipe in an exhaust gas recirculation mechanism which recirculates part of the exhaust gas G to be discharged from the internal combustion engine to the exhaust pipe 7, to an intake pipe of the internal combustion engine, can be used.

[Sensor Element 2]

Figure 5:
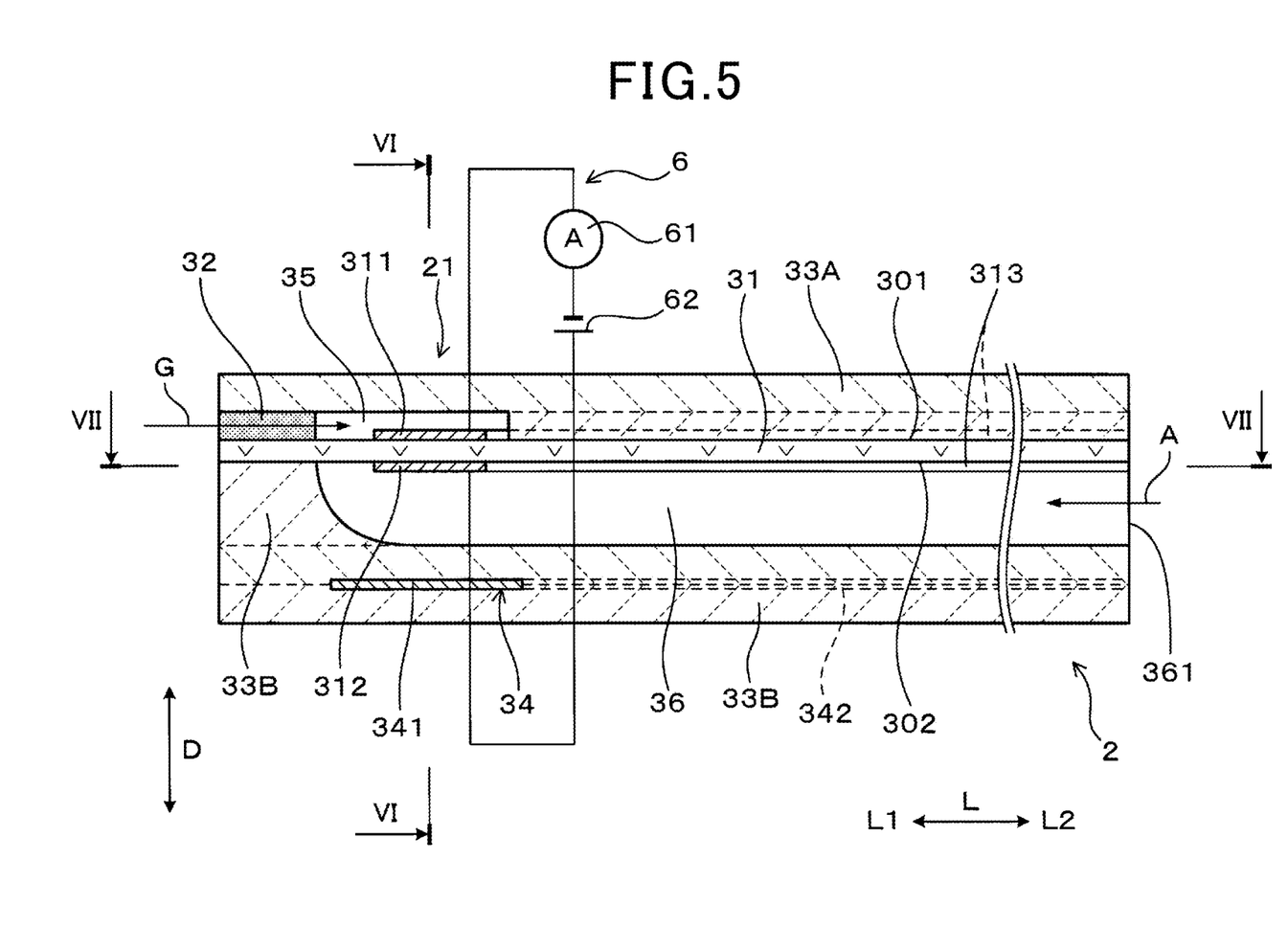
FIG. 5 is an explanatory diagram illustrating an enlarged cross-section of a sensor element of the gas sensor according to the embodiment.
Figure 6:
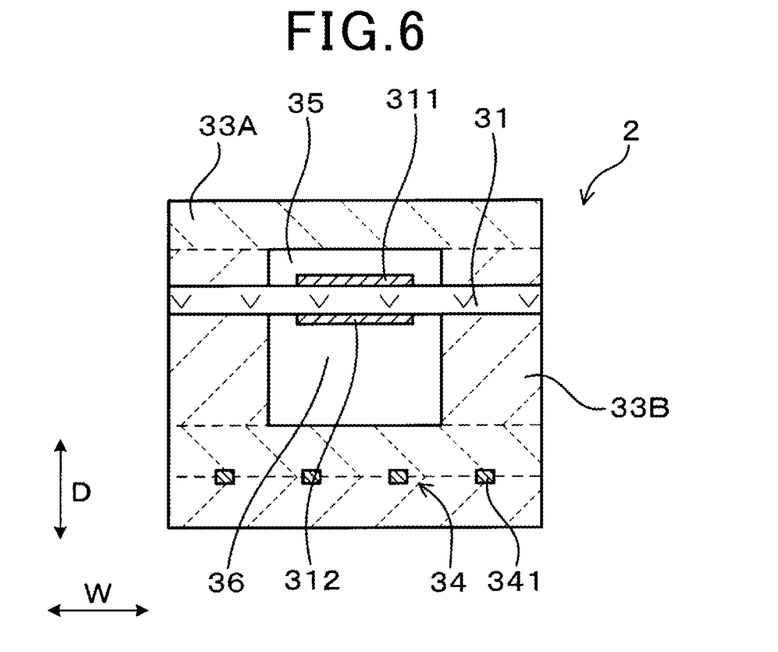
FIG. 6 is an explanatory diagram illustrating a cross-section VI-VI in FIG. 5.

As illustrated in FIG. 5 and FIG. 6, the sensor element 2 of the present embodiment is formed in an elongated rectangular shape and includes a solid electrolyte body 31, an exhaust electrode 311, an atmospheric electrode 312, a first insulating body 33A, a second insulating body 33B, a gas chamber 35, an atmospheric duct 36 and a heating element 34. The sensor element 2 is a laminate-type sensor element in which the respective insulating bodies 33A and 33B and the heating element 34 are laminated on the solid electrolyte body 31.

In the present embodiment, the axial direction L of the sensor element 2 refers to a direction in which the sensor element 2 extends in an elongated shape. Further, a direction which is orthogonal to the axial direction L and in which the solid electrolyte body 31 and the respective insulating bodies 33A and 33B are laminated, that is, in which the solid electrolyte body 31, the respective insulating bodies 33A and 33B and the heating element 34 are laminated will be referred to as a lamination direction D. Further, a direction which is orthogonal to the axial direction L and the lamination direction D will be referred to as a width direction W. Further, a side exposed to the exhaust gas G in the axial direction L of the sensor element 2 refers to a distal end side L1, and an opposite side of the distal end side L1 will be referred to as a base end side L2.

[Solid Electrolyte Body 31, Exhaust Electrode 311 and Atmospheric Electrode 312]

As illustrated in FIG. 5 and FIG. 6, the solid electrolyte body 31 has conductivity of oxide ions ($O^{2-}$) at a predetermined activation temperature. The exhaust electrode 311 to be exposed to the exhaust gas G is provided on a first surface 301 of the solid electrolyte body 31, and the atmospheric electrode 312 to be exposed to atmospheric air A is provided on a second surface 302 of the solid electrolyte body 31. The exhaust electrode 311 and the atmospheric electrode 312 are disposed at positions at which the exhaust electrode 311 overlaps with the atmospheric electrode 312 via the solid electrolyte body 31 in the lamination direction D at a portion on the distal end side L1 to be exposed to the exhaust gas G in the axial direction L of the sensor element 2. At a portion on the distal end side L1 in the axial direction L of the sensor element 2, the detection unit 21 is formed by the exhaust electrode 311 and the atmospheric electrode 312, and a portion of the solid electrolyte body 31 disposed between these electrodes 311 and 312. The first insulating body 33A is laminated on the first surface 301 of the solid electrolyte body 31, and the second insulating body 33B is laminated on the second surface 302 of the solid electrolyte body 31.

The solid electrolyte body 31 is formed with zirconia oxide, contains zirconia (equal to or greater than 50 mass %) as a main component and is formed with stabilized zirconia or partially stabilized zirconia in which rare earth metal elements or alkali earth metal elements are substituted in part of the zirconia. Yttria, scandia or calcia can be substituted for part of zirconia which constitutes the solid electrolyte body 31.

The exhaust electrode 311 and the atmospheric electrode 312 contain platinum as a noble metal which exhibits catalyst activity with respect to oxygen and zirconia oxide as a common material with the solid electrolyte body 31. The common material is provided to maintain coupling strength between the exhaust electrode 311 and the atmospheric electrode 312 which are formed with an electrode material, and the solid electrolyte body 31 when a paste-like electrode material is printed (applied) on the solid electrolyte body 31 and the solid electrolyte body 31 and the electrode material are fired.

As illustrated in FIG. 5, an electrode lead portion 313 for electrically connecting these electrodes 311 and 312 to outside of the gas sensor 1 is connected to the exhaust electrode 311 and the atmospheric electrode 312. The electrode lead portion 313 is drawn to a portion on the base end side L2 in the axial direction L of the sensor element 2.

[Gas Chamber 35]

As illustrated in FIG. 5 and FIG. 6, a gas chamber 35 which is surrounded by the first insulating body 33A and the solid electrolyte body 31 is formed adjacent to the first insulator 33A and the solid electrolyte body 31 on the first surface 301 of the solid electrolyte body 31. The gas chamber 35 is formed at a portion on the distal end side L1 in the axial direction L of the first insulating body 33A so as to accommodate the exhaust electrode 311. The gas chamber 35 is formed as a space enclosed by the first insulating body 33A, a diffusion resistance portion 32 and the solid electrolyte body 31. The exhaust gas G flowing through the exhaust pipe 7 passes through the diffusion resistance portion 32 and is introduced into the gas chamber 35.

[Diffusion Resistance Portion 32]

As illustrated in FIG. 5, the diffusion resistance portion 32 of the present embodiment is provided adjacent to the gas chamber 35 on the distal end side L1 in the axial direction L of the gas chamber 35. The diffusion resistance portion 32 is disposed inside an inlet which is open adjacent to the gas chamber 35 on the distal end side L1 in the axial direction L of the gas chamber 35 at the first insulating body 33A. The diffusion resistance portion 32 is formed with porous metal oxide such as alumina. A diffusion rate (flow rate) of the exhaust gas G to be introduced into the gas chamber 35 is determined by a rate at which the exhaust gas G passes through pores at the diffusion resistance portion 32 being limited.

The diffusion resistance portion 32 may be formed adjacent to the gas chamber 35 on both sides in the width direction W of the gas chamber 35. In this case, the diffusion resistance portion 32 is disposed inside an inlet which is open adjacent to gas chamber 35 on the both sides in the width direction W of the gas chamber 35 at the first insulating body 33A. Note that the diffusion resistance portion 32 can be formed using pin holes which are small through holes communicated with the gas chamber 35, as well as being formed using a porous body.

[Atmospheric Duct 36]

Figure 7:
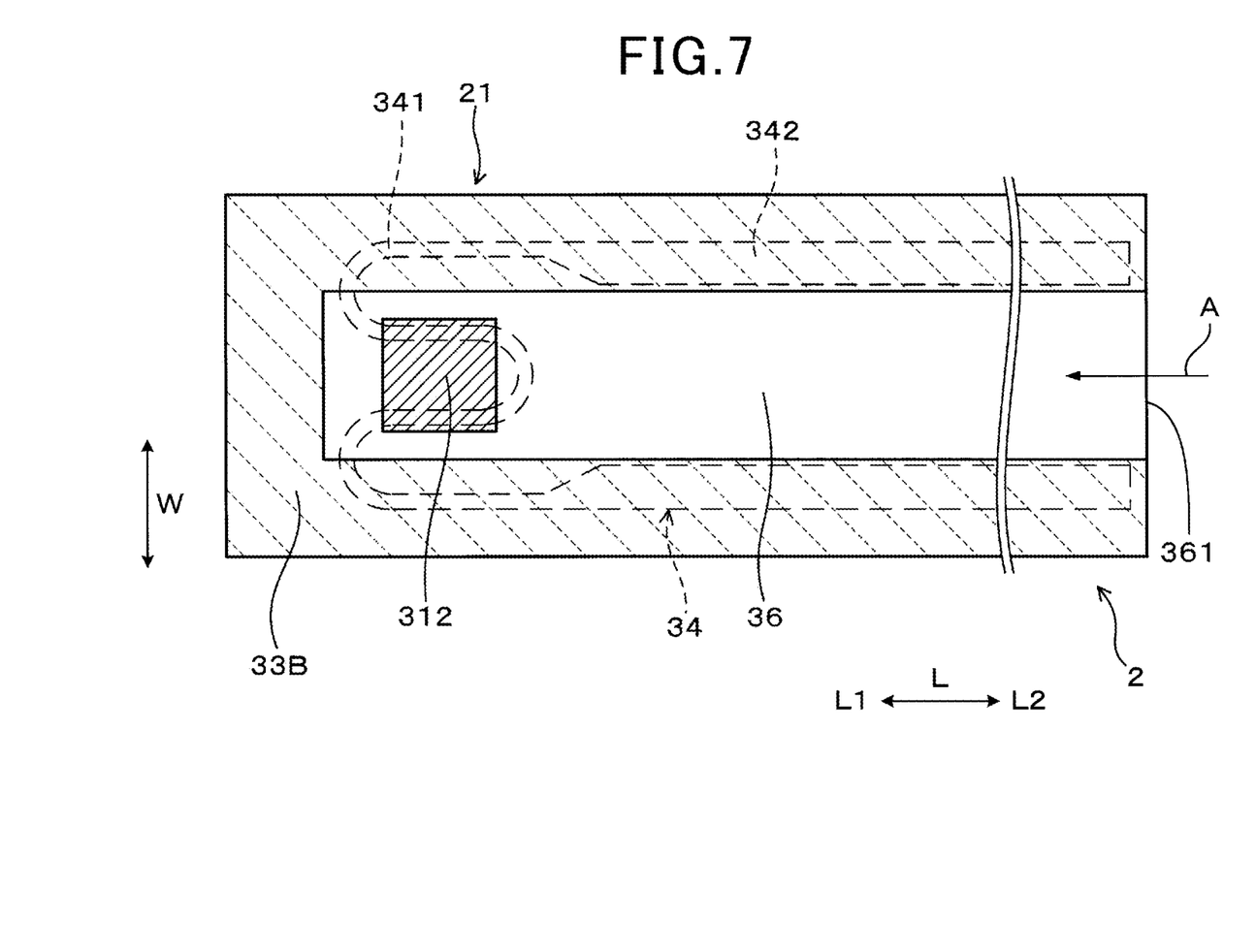
FIG. 7 is an explanatory diagram illustrating a cross-section VII-VII in FIG. 5.

As illustrated in FIG. 5 to FIG. 7, the atmospheric duct 36 which is surrounded by the second insulating body 33B and the solid electrolyte body 31 is formed on the second surface 302 of the solid electrolyte body 31 adjacent to the second insulating body 33B and the solid electrolyte body 31. The atmospheric duct 36 is formed from a portion in the axial direction L, which accommodates the atmospheric electrode 312 at the second insulating body 33B to a base end position to be exposed to the atmospheric air A in the axial direction L of the sensor element 2. A base end opening 361 as an atmosphere introduction portion of the atmospheric duct 36 is formed at a base end position in the axial direction L of the sensor element 2. The atmospheric duct 36 is formed from the base end opening 361 to a position where the atmospheric duct 36 overlaps with the gas chamber 35 via the solid electrolyte body 31 in the lamination direction D. The atmospheric air A is introduced into the atmospheric duct 36 from the base end opening 361.

[Heating Element 34]

As illustrated in FIG. 5 to FIG. 7, the heating element 34, which is buried inside the second insulating body 33B which forms the atmospheric duct 36, includes a heating portion 341 heated through energization, and a heating element lead portion 342 leading to the heating portion 341. The heating portion 341 is disposed at a position where at least part of the heating portion 341 overlaps with the exhaust electrode 311 and the atmospheric electrode 312 in the lamination direction D of the solid electrolyte body 31 and the respective insulating bodies 33A and 33B.

Further, the heating element 34 includes the heating portion 341 heated by energization, and a pair of heating element lead portions 342 leading to the base end side L2 in the axial direction L of the heating portion 341. The heating portion 341 is formed with a linear conductor portion which meanders by a linear portion and a curved portion. The linear portion of the heating portion 341 of the present embodiment is formed parallel to the axial direction L. The heating element lead portion 342 is formed with a linear conductor portion which is parallel to the axial direction L. A resistance value per unit length of the heating portion 341 is greater than a resistance value per unit length of the heating element lead portion 342. The heating element lead portion 342 is drawn from the heating portion 341 to a portion on the base end side L2 in the axial direction L. The heating element 34 contains a metal material having conductivity.

As illustrated in FIG. 5 and FIG. 7, the heating portion 341 of the present embodiment is formed in a shape which meanders in the axial direction L at a position on the distal end side L1 in the axial direction L at the heating element 34. Note that the heating portion 341 may be formed so as to meander in the width direction W. The heating portion 341 is disposed at a position facing the exhaust electrode 311 and the atmospheric electrode 312 in the lamination direction D which is orthogonal to the axial direction L. In other words, the heating portion 341 is disposed at a position where the heating portion 341 overlaps with the exhaust electrode 311 and the atmospheric electrode 312 in the lamination direction D at a portion on the distal end side L1 in the axial direction L of the sensor element 2.

A cross-sectional area of the heating portion 341 is smaller than a cross-sectional area of the heating element lead portion 342, and a resistance value per unit length of the heating portion 341 is higher than a resistance value per unit length of the heating element lead portion 342. This cross-sectional area refers to a cross-sectional area of a surface which is orthogonal in a direction in which the heating portion 341 and the heating element lead portion 342 extend. Further, if a voltage is applied to the pair of heating element lead portions 342, the heating portion 341 is heated by Joule heat, and a portion around the detection unit 21 is heated at a target temperature by this heat.

[Respective Insulating Bodies 33A and 33B]

As illustrated in FIG. 5 and FIG. 6, the first insulating body 33A forms the gas chamber 35, the second insulating body 33B forms the atmospheric duct 36, and the heating element 34 is buried in the second insulating body 33B. The first insulating body 33A and the second insulating body 33B are formed with metal oxide such as alumina (aluminum oxide). The respective insulating bodies 33A and 3B are formed as a dense body through which the exhaust gas G or the atmospheric air A cannot pass, and few pores through which a gas can pass are formed at the respective insulating bodies 33A and 33B.

[Terminal Portion 22 of Sensor Element 2]

As illustrated in FIG. 1, the terminal portions 22 of the sensor element 2 are electrically connected to the respective electrode lead portions 313 of the exhaust electrode 311 and the atmospheric electrode 312 and the proximal end portion in the axial direction L of a pair of the heating element lead portions 342. The terminal portions 22 are disposed on both side surfaces at the proximal end portion in the axial direction L of the sensor element 2. The proximal end portions in the axial direction L of the respective electrode lead portions 313 and the heating element lead portions 342 are connected to the terminal portions 22 via through holes formed at the respective insulating bodies 34A and 34B.

[Porous Layer 37]

As illustrated in FIG. 1, a porous layer 37 for capturing poisoning substances with respect to the exhaust electrode 311, condensed water generated in the exhaust pipe 7, or the like, is provided at the entire circumference of a portion on the distal end side L1 in the axial direction L of the sensor element 2. The porous layer 37 is formed with porous ceramics (metal oxide) such as alumina. A porosity of the porous layer 37 is greater than a porosity of the diffusion resistance portion 32, and a flow volume of the exhaust gas G which can pass through the porous layer 37 is greater than a flow volume of the exhaust gas G which can pass through the diffusion resistance portion 32.

Here, as illustrated in FIG. 1 and FIG. 4, a direction which is orthogonal to the axial direction L of the sensor element 2 and which extends in a radial manner from a central axis line of the sensor element 2, at the gas sensor 1 of the present embodiment will be referred to as a radial direction R. The central axis line refers to a virtual line which passes through the center of a figure of a cross-section which is orthogonal to the axial direction L of the sensor element 2.

[Housing 41]

Figure 3:
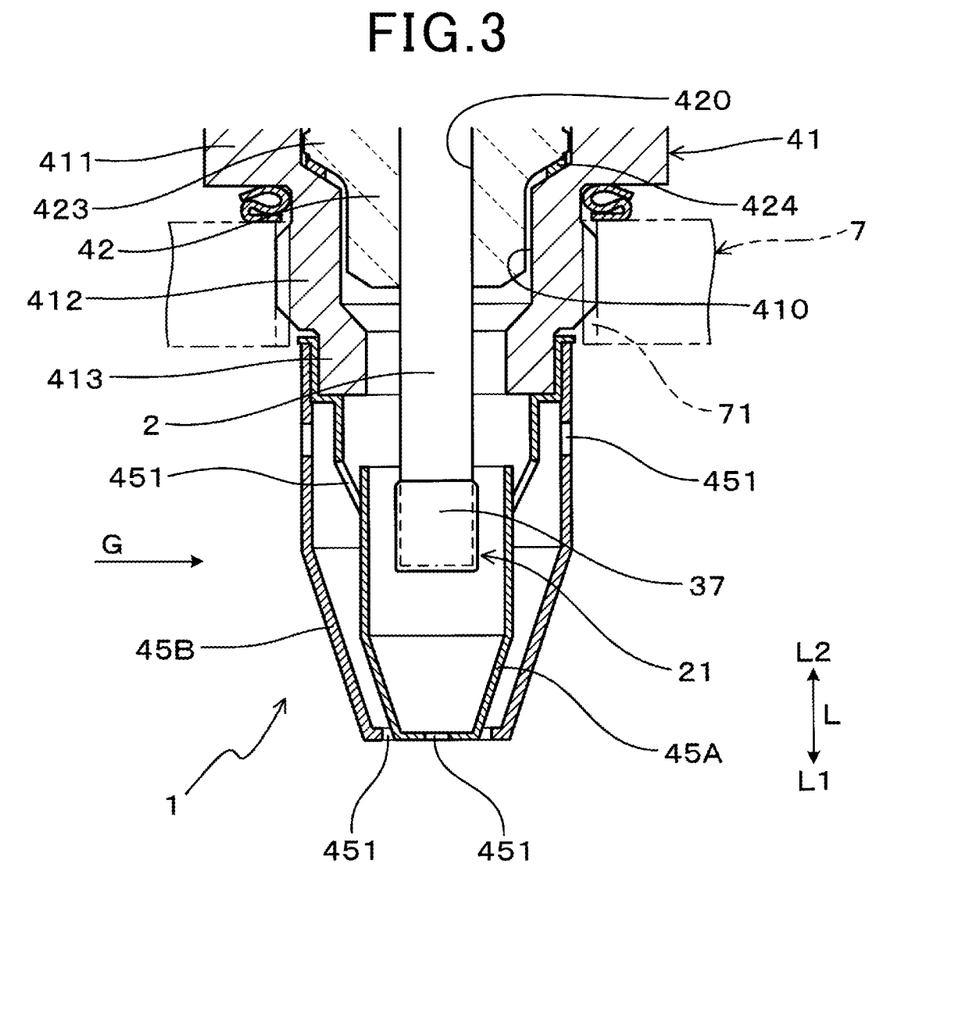
FIG. 3 is an explanatory diagram illustrating an enlarged cross-section of a distal end potion in the axial direction of the gas sensor in FIG. 1.

As illustrated in FIG. 1 to FIG. 3, the housing 41 is used to tighten the gas sensor 1 on the mounting port 71 of the exhaust pipe 7. The housing 41 includes a flange portion 411 which constitutes a maximum outer diameter portion, a distal end side cylindrical portion 412 formed on the distal end side L1 in the axial direction L of the flange portion 411, and a base end side cylindrical portion 414 formed on the base end side L2 in the axial direction L of the flange portion 411. The "maximum outer diameter portion" indicates a portion at which a radial dimension in the radial direction R is the largest, of the housing 41. The outer periphery of the flange portion 411 is formed in a hexagonal shape to be utilized when the gas sensor 1 is tightened on the mounting port 71 by a tool. The distal end side cylindrical portion 412 and the base end side cylindrical portion 414 are formed in a cylindrical shape.

An external thread to be tighten on an internal thread at the mounting port 71 is formed at the outer periphery of a portion on the base end side L2 in the axial direction L of the distal end side cylindrical portion 412. A mounting portion 413 at which distal end side covers 45A and 45B which will be described later are to be mounted is formed at a portion on the distal end side L1 in the axial direction L of the distal end side cylindrical portion 412. A swage portion 415 bent on the inner periphery side is formed at the base end side cylindrical portion 414. Note that there is also a case where the swage portion 415 is not formed at the base end side cylindrical portion 414 depending on structures of a first insulator 42 and a second insulator 43.

[Inner Periphery Side Cover 5]

As illustrated in FIG. 1 and FIG. 2, the inner periphery side cover 5 is provided to absorb heat from the housing 41 and to suppress transfer of heat from the housing 41 to the sealing member 47 located at the end portion on the base end side L2 in the axial direction L of the gas sensor 1. The inner periphery side cover 5 includes a cylindrical body portion 51 in a cylindrical shape, and a bent portion 52 which is bent on the inner periphery side in the radial direction R at the proximal end portion in the axial direction L of the cylindrical body portion 51. In other words, the bent portion 52 which is bent on the inner periphery side with respect to the cylindrical body portion 51 of the inner periphery side cover 5 and which is in indirect contact with an end surface on the base end side L2 in the axial direction L of the second insulator 43 is formed at the proximal end portion in the axial direction L of the inner periphery side cover 5.

The bent portion 52 is perpendicularly bent on the inner periphery side in the radial direction R from the cylindrical body portion 51. A metal swage member 431 is disposed between the bent portion 52 and an end surface on the base end side L2 in the axial direction L of the second insulator 43. The swage member 431 is constituted with a leaf spring and has spring characteristics which causes repulsion after elastic deformation. As a result of the bent portion 52 of the inner periphery side cover 5 being bent on the inner periphery side in the radial direction R, the second insulator 43 can be fixed at the first insulator 42 in a state where the spring characteristics of the swage member 431 are provided to the second insulator 43.

The distal end portion in the axial direction L of the cylindrical body portion 51 of the inner periphery side cover 5 is in contact with the housing 41 and the outer periphery side covers 46A and 46B, while the bent portion 52 of the inner periphery side cover 5 is not in contact with the outer periphery side covers 46A and 46B. The bent portion 52 is in indirect contact with the second insulator 43 via the swage member 431. As a result of the bent portion 52 of the inner periphery side cover 5 being bent on the inner periphery side in the radial direction R and being in indirect contact with the second insulator 43 via the swage member 431, heat to be transferred from the housing 41 to the cylindrical body portion 51 of the inner periphery side cover 5 can be released to the second insulator 43 from the bent portion 52 of the inner periphery side cover 5. Note that the bent portion 52 of the inner periphery side cover 5 may be in direct contact with the second insulator 43.

The distal end portion in the axial direction L of the inner periphery side cover 5 is mounted on the outer periphery of the base end side cylindrical portion 414 of the housing 41. The distal end portion in the axial direction L of the inner periphery side cover 5 of the present embodiment is bonded to the outer periphery of the base end side cylindrical portion 414 of the housing 41 through welding, or the like. Further, the base end side cylindrical portion 414 of the housing 41 can be pressed into the distal end portion in the axial direction L of the inner periphery side cover 5 other than being bonded through welding. Further, the distal end portion in the axial direction L of the inner periphery side cover 5 can be swaged and fixed at the outer periphery of the base end side cylindrical portion 414 of the housing 41.

[Outer Periphery Side Covers 46A and 46B]

As illustrated in FIG. 1 and FIG. 2, the outer periphery side covers 46A and 46B are provided to cover a wiring portion located on the base end side L2 in the axial direction L of the gas sensor 1 to protect this wiring portion from water, or the like, in the atmospheric air A. The wiring portion is constituted with the contact terminals 44, connection portions (connection metal fittings 441) of the contact terminals 44 and the lead wires 48, and the like, as portions which are electrically connected to the sensor element 2.

The outer periphery side covers 46A and 46B are formed as two parts to provide a water-repellent filter 462 which prevents water in the atmospheric air A from entering the gas sensor 1, between the outer periphery side covers 46A and 46B. Specifically, the outer periphery side covers 46A and 46B of the present embodiment include a first outer periphery side cover 46A disposed on the outer periphery side of the inner periphery side cover 5, and a second outer periphery side cover 46B mounted at a portion on the base end side L2 in the axial direction L of the first outer periphery side cover 46A. A portion on the distal end side L1 in the axial direction L of the second outer periphery side cover 46B is mounted on an outer periphery at a portion on the base end side L2 in the axial direction L of the first outer periphery side cover 46A.

The sealing member 47 which holds a plurality of lead wires 48 is held on the inner periphery side of the portion on the base end side L2 in the axial direction L of the second outer periphery side cover 46B. The water-repellent filter 462 is disposed between the first outer periphery side cover 46A and the second outer periphery side cover 46B, and between the second outer periphery side cover 46B and the sealing member 47.

As illustrated in FIG. 2, a portion on the distal end side L1 in the axial direction L of the second outer periphery side cover 46B is swaged at the portion on the base end side L2 in the axial direction L of the first outer periphery side cover 46A by a recessed portion 463 which is recessed from the outer periphery side to the inner periphery side. Further, an intermediate portion in the axial direction L of the second outer periphery side cover 46B is swaged at the portion on the base end side L2 in the axial direction L of the first outer periphery side cover 46A by a recessed portion 464 which is recessed from the outer periphery side to the inter periphery side in a state where the water-repellent filter 462 is disposed between the second outer periphery side cover 46B and the first outer periphery side cover 46A. Further, a portion on the base end side L2 in the axial direction L of the second outer periphery side cover 46B is swaged at the sealing member 47 by a recessed portion 465 which is recessed from the outer periphery side to the inner periphery side in a state where the water-repellent filter 462 is disposed between the second outer periphery side cover 46B and the sealing member 47.

The inner periphery side cover 5 and the outer periphery side covers 46A and 46B are disposed outside the exhaust pipe 7 of the internal combustion engine. The gas sensor 1 of the present embodiment is an in-vehicle gas sensor, and a vehicle body at which the exhaust pipe 7 is disposed is connected to an engine compartment at which the internal combustion engine is disposed. Further, atmosphere (air) A in the engine compartment flows around the inner periphery side cover 5 and the outer periphery side covers 46A and 46B.

An atmosphere introduction hole 461 for introducing the atmospheric air A from outside the gas sensor 1 is formed at the second outer periphery side cover 46B. The water-repellent filter 462 is disposed so as to cover the atmosphere introduction hole 461 from the inter periphery side of the second outer periphery side cover 46B. The base end opening 361 of the atmospheric duct 36 at the sensor element 2 is open to space inside the inner periphery side cover 5 and the outer periphery side covers 46A and 46B. The atmospheric air A existing around the atmosphere introduction hole 461 of the second outer periphery side cover 46B is taken in the inner periphery side cover 5 and the outer periphery side covers 46A and 46B by way of the water-repellent filter 462. Then, the atmospheric air A which passes through the water-repellent filter 462 flows from the base end opening 361 of the atmospheric duct 36 of the sensor element 2 into the atmospheric duct 36 and is introduced to the atmospheric electrode 312 inside the atmospheric duct 36.

[Thicknesses t1 and t2 of Inner Periphery Side Cover 5 and Outer Periphery Side Covers 46A and 46B]

As illustrated in FIG. 2 and FIG. 4, a second thickness t2 in the radial direction R of the inner periphery side cover 5 is greater than a first thickness t1 in the radial direction R of the outer periphery side covers 46A and 46B. The inner periphery side cover 5 is formed to be as thick as possible to have a function as a heat dissipation portion for releasing heat from the housing 41. The second thickness t2 of the inner periphery side cover 5 can be made two to five times as thick as the first thickness t1 of the outer periphery side covers 46A and 46B. As a result of the second thickness t2 of the inner periphery side cover 5 being greater than the first thickness t1 of the outer periphery side covers 46A and 46B, a heat transfer amount from the housing 41 to the inner periphery side cover 5 can be made greater than a heat transfer amount from the housing 41 to the outer periphery side covers 46A and 46B. This can suppress transfer of heat from the housing 41 to the outer periphery side covers 46A and 46B to the sealing member 47.

The second thickness t2 of the inner periphery side cover 5 of the present embodiment is uniform over the entire length in the axial direction L. The first thickness t1 of the outer periphery side covers 46A and 46B partially changes. In other words, a thickness of the portion on the base end side L2 in the axial direction L of the first outer periphery side cover 46A is greater than thicknesses of other portions. Further, the thickness of the second outer periphery side cover 46B is uniform over the entire length in the axial direction L.

In a case where the second thickness t2 of the inner periphery side cover 5 is not uniform, an average value of the second thickness t2 of the inner periphery side cover 5 can be used as the second thickness t2 of the inner periphery side cover 5 to be compared with the first thickness t1 of the outer periphery side covers 46A and 46B. Further, in a case where the second thickness t2 of the inner periphery side cover 5 is not uniform, a minimum value of the second thickness t2 of the inner periphery side cover 5 can be used as the second thickness t2 of the inner periphery side cover 5 to be compared with the first thickness t1 of the outer periphery side covers 46A and 46B.

In a case where the first thickness t1 of the outer periphery side covers 46A and 46B is not uniform, an average value of the first thickness t1 of the outer periphery side covers 46A and 46B can be used as the first thickness t1 of the outer periphery side covers 46A and 46B to be compared with the second thickness t2 of the inner periphery side cover 5. Further, in a case where the first thickness t1 of the outer periphery side covers 46A and 46B is not uniform, a minimum value of the first thickness t1 of the outer periphery side covers 46A and 46B can be used as the first thickness t1 of the outer periphery side covers 46A and 46B to be compared with the second thickness t2 of the inner periphery side cover 5.

Further, the second thickness t2 of the inner periphery side cover 5 can be compared with the first thickness t1 of the outer periphery side covers 46A and 46B at portions where the inner periphery side cover 5 faces the outer periphery side covers 46A and 46B. In other words, a thickness of the cylindrical body portion 51 of the inner periphery side cover 5 can be made greater than a thickness of a portion on the outer periphery side of the cylindrical body portion 51 of the outer periphery side covers 46A and 46B.

[Substantially Cylindrical Space 50]

As illustrated in FIG. 1 and FIG. 2, the substantially cylindrical space 50 is formed as a predetermined gap (interval) between the inner periphery side cover 5 and the outer periphery side cover 46A. The substantially cylindrical space 50 forms a heat insulating layer of the air (atmosphere) A between the inner periphery side cover 5 and the outer periphery side cover 46A. As a result of the substantially cylindrical space 50 being formed, heat transferred from the housing 41 to the inner periphery side cover 5 can be prevented from being transferred from the inner periphery side cover 5 to the outer periphery side covers 46A and 46B.

The entire circumference of the portion on the distal end side L1 in the axial direction L of the outer periphery side cover 46A is in contact with the entire circumference of the portion on the distal end side L1 in the axial direction L of the inner periphery side cover 5. The entire circumference of the portion on the distal end side L1 in the axial direction L of the outer periphery side cover 46A of the present embodiment is bonded to the entire circumference of the portion on the distal end side L1 in the axial direction L of the inner periphery side cover 5 through welding, or the like. Note that when laser welding, or the like, is performed, the outer periphery side cover 46A, the inner periphery side cover 5 and the housing 41 can be bonded at the same time by melting the portion on the distal end side L1 in the axial direction L of the outer periphery side cover 46A and the portion on the distal end side L1 in the axial direction L of the inner periphery side cover 5 and also melting the base end side cylindrical portion 414 of the housing 41.

As a result of the entire circumference of the portion on the distal end side L1 in the axial direction L of the outer periphery side cover 46A being bonded to the entire circumference of the portion on the distal end side L1 in the axial direction L of the inner periphery side cover 5, an end portion 501 on the distal end side L1 in the axial direction L of the substantially cylindrical space 50 is closed. Further, the portion on the distal end side L1 in the axial direction L of the inner periphery side cover 5 can be also pressed into the inner periphery side of the portion on the distal end side L1 in the axial direction L of the outer periphery side cover 46A. Further, the portion on the distal end side L1 in the axial direction L of the outer periphery side cover 46A can be also swaged and fixed at the portion on the distal end side L1 in the axial direction L of the inner periphery side cover 5.

The portion on the base end side L2 in the axial direction L of the inner periphery side cover 5 is disposed on the inner periphery side of the outer periphery side covers 46A and 46B. In other words, the portion on the base end side L2 in the axial direction L of the inner periphery side cover 5 is disposed at a position on the inner periphery side, which is separate from the outer periphery side cover 46A. By this means, an opening 502 on the base end side L2 in the axial direction L of the substantially cylindrical space 50 is open. This configuration causes heat to be transferred between the inner periphery side cover 5 and the outer periphery side cover 46A mostly at the portion on the distal end side L1 in the axial direction L. This can suppress heat transfer from the inner periphery side cover 5 to the sealing member 47.

[Other Structures of Outer Periphery Side Cover 46A]

Figure 8:
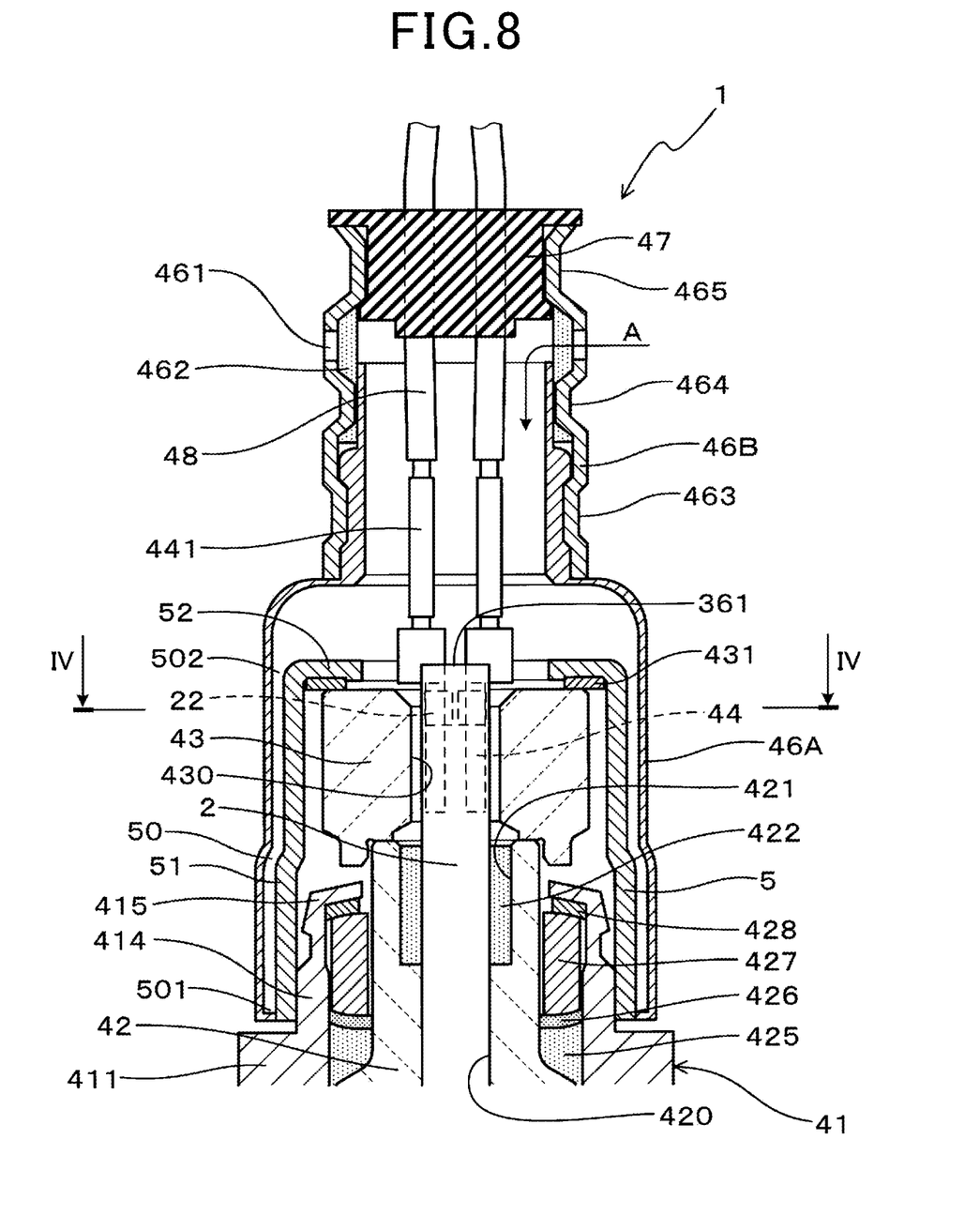
FIG. 8 is an explanatory diagram illustrating an enlarged cross-section of a proximal end portion in an axial direction of gas sensors according to another embodiment.

As illustrated in FIG. 8, the entire circumference of the distal end portion in the axial direction L of the outer periphery side cover 46A may be bent on the inner periphery side in the radial direction R and may be in contact with the entire circumference of the outer periphery of the cylindrical body portion 51 of the inner periphery side cover 5. In this case, the end portion 501 on the distal end side L1 in the axial direction L of the substantially cylindrical space 50 is closed by the outer periphery side cover 46A and the inner periphery side cover 5, and the substantially cylindrical space 50 can be made to reach the distal end portion in the axial direction L of the inner periphery side cover 5. Further, the substantially cylindrical space 50 can be formed to be as long as possible in the axial direction L.

[First Insulator 42]

As illustrated in FIG. 1 to FIG. 3, the first insulator 42 is disposed inside a center hole 410 which penetrates a central portion of the housing 41 in the axial direction L. The first insulator 42 is also referred to as a first insulator and is constituted with an insulating ceramic material. A first insertion hole 420 which penetrates the first insulator 42 in the axial direction L is formed at a central portion of the first insulator 42 so as to allow the sensor element 2 to be inserted. A recessed portion 421 for fixing at which glass powder 422 for fixing the sensor element 2 is to be disposed is formed at an end portion on the base end side L2 in the axial direction L of the first insertion hole 420. The sensor element 2 is fixed at the first insulator 42 by the glass powder 422 disposed at the recessed portion 421 for fixing in a state where the sensor element 2 is inserted into the first insertion hole 420 of the first insulator 42.

A projecting portion 423 which forms a maximum outer diameter portion at the first insulator 42 is formed at the outer periphery of the first insulator 42. A seal material 424 is disposed on the distal end side L1 in the axial direction L of the projecting portion 423 at a center hole 410 in a state where the first insulator 42 is disposed at the center hole 410 of the housing 41, and swage materials 425, 426, 427 and 426 are disposed on the base end side L2 in the axial direction L of the projecting portion 423 at the center hole 410. The swage materials 425, 426, 427 and 428 can include a powder seal material 425, an annular plate packing 426, a cylindrical body 427 and a swage material 428. As a result of the swage portion 415 of the base end side cylindrical portion 414 of the housing 41 being bent on the inner periphery side in the radial direction R, the first insulator 42 is swaged and fixed inside the center hole 410 of the housing 41 via the seal material 424 and the swage materials 425, 426, 427 and 428.

[Second Insulator 43]

As illustrated in FIG. 2 and FIG. 4, the second insulator 43 is disposed on the base end side L2 in the axial direction L of the first insulator 42 and holds the contact terminals 44 which are in contact with the terminal portions 22 of the sensor element 2. The second insulator 43 is also referred to as a second insulator and is constituted with an insulating ceramic material. A second insertion hole 430 which allows the sensor element 2 to be inserted is formed at a central portion of the second insulator 43 so as to pierce through the second insulator 43 in the axial direction L. A groove portion 432 at which the contact terminals 44 are to be disposed is formed at a position which is communicated with the second insertion hole 430 at the second insulator 43. The second insulator 43 is disposed on the inner periphery side in the radial direction R of the inner periphery side cover 5 and the outer periphery side cover 46A.

[Contact Terminal 44]

As illustrated in FIG. 2 and FIG. 4, the contact terminals 44 are in contact with the terminal portions 22 of the sensor element 2 and electrically connect the terminal portions 22 to the lead wires 48. The contact terminals 44 are disposed at the groove portion 432 of the second insulator 43. The contact terminals 44 are connected to the lead wires 48 via connection metal fittings 441 and are in contact with the terminal portions 22 by exerting restoring force of elastic deformation. A plurality of contact terminals 44 corresponding to the number of terminal portions 22 at the sensor element 2, that is, the number of the exhaust electrode 311, the atmospheric electrode 312, the respective electrode lead portions 313, and the pair of heating element lead portions 342 illustrated in FIG. 5, are disposed.

[Sealing Member 47 and Lead Wire 48]

As illustrated in FIG. 1 and FIG. 2, the sealing member (bush) 47 is disposed on the inner periphery side of the second outer periphery side cover 46B and seals and holds a plurality of lead wires 48. The sealing member 47 is constituted with a rubber material which can elastically deform to provide a function as a seal material. Through holes into which the lead wires 48 are inserted are formed at the sealing member 47. As a result of the second outer periphery side cover 46B being swaged at the sealing member 47, respective gaps between the respective lead wires 48 and the respective through holes, and between the sealing member 47 and the second outer periphery side cover 46B are sealed. The lead wires 48 are provided to connect the respective contact terminals 44 to a sensor control device 6 outside the gas sensor 1. The lead wires 48 are formed by covering internal conductors with an overcoat layer.

[Distal End Side Covers 45A and 45B]

As illustrated in FIG. 3, the distal end side covers 45A and 45B project on the distal end side L1 from an end surface on the distal end side L1 in the axial direction L of the housing 41 and cover the detection unit 21 of the sensor element 2. The distal end side covers 45A and 45B are mounted on the outer periphery of the mounting portion 413 formed at the distal end side cylindrical portion 412 of the housing 41. The distal end side covers 45A and 45B of the present embodiment have a double structure including the first distal end side cover 45A and the second distal end side cover 45B which covers the first distal end side cover 45A. Gas flow holes 451 through which the exhaust gas G can flow are formed at the first distal end side cover 45A and the second distal end side cover 45B.

The detection unit 21 of the sensor element 2 and the distal end side covers 45A and 45B are disposed inside the exhaust pipe 7 of the internal combustion engine. Part of the exhaust gas G flowing inside the exhaust pipe 7 flows into the distal end side covers 45A and 45B from the gas flow holes 451 of the distal end side covers 45A and 45B. Then, the exhaust gas G inside the distal end side covers 45A and 45B passes through the porous layer 37 and the diffusion resistance portion 32 of the sensor element 2 and is introduced to the exhaust electrode 311. Note that the distal end side covers 45A and 45B may have a single structure in which the gas flow holes 451 are formed.

[Sensor Control Device 6]

As illustrated in FIG. 1, the lead wires 48 at the gas sensor 1 are electrically connected to the sensor control device 6 which controls gas detection at the gas sensor 1. The sensor control device 6 performs electric control at the gas sensor 1 in coordination with an engine control device which controls combustion operation at the engine. As illustrated in FIG. 5, a current measurement circuit 61 which measures a current flowing between the exhaust electrode 311 and the atmospheric electrode 312, a voltage application circuit 62 which applies a voltage between the exhaust electrode 311 and the atmospheric electrode 312, an energization circuit for energizing the heating element 34, or the like, are formed at the sensor control device 6. Note that the sensor control device 6 may be constructed inside the engine control device.

[Other Gas Sensors 1]

The gas sensor 1 may detect concentration of specific gas components such as NOx (nitrogen oxide), or the like. At an NOx sensor, a pump electrode which pumps oxide to the atmospheric electrode 312 by application of a voltage is disposed on an upstream side of flow of the exhaust gas G, which is in contact with the exhaust electrode 311 at the solid electrolyte body 31. The atmospheric electrode 312 is also formed at a position where the atmospheric electrode 312 overlaps with the pump electrode via the solid electrolyte body 31 in the lamination direction D.

The gas sensor 1 may be a sensor which includes a cup-type sensor element 2 which has the solid electrolyte body 31 formed in a bottomed cylindrical shape, other than a sensor which includes a laminate-type sensor element 2. At the cup-type sensor element 2, the exhaust electrode 311 is provided on an outer periphery surface of the solid electrolyte body 31, and the atmospheric electrode 312 is provided on an inner periphery surface of the solid electrolyte body 31. Further, the cup-type sensor element 2 is disposed at the center hole 410 of the housing 41 without using the first insulator 42. Also in this case, the inner periphery side cover 5 and the outer periphery side cover 46A can be mounted on the outer periphery of the base end side cylindrical portion 414 of the housing 41.

[Operational Effects]

At the gas sensor 1 of the present embodiment, the inner periphery side cover 5 is disposed on the inner periphery side in the radial direction R of the outer periphery side covers 46A and 46B which hold the sealing member 47. The substantially cylindrical space 50 which functions as a heat insulating layer is formed between the inner periphery side cover 5 and the outer periphery side covers 46A and 46B, and the inner periphery side cover 5 and the outer periphery side covers 46A and 46B are in contact with each other only at distal end portions in the axial direction L. Further, a heat transfer path which passes through the inner periphery side cover 5 and a heat transfer path which passes through the outer periphery side covers 46A and 46B are formed from the housing 41 to the base end side L2 in the axial direction L.

A temperature of the exhaust gas G which passes inside the exhaust pipe 7 of the internal combustion engine becomes high, for example, approximately from 1000 to 1100° C. by combustion of a fuel in the internal combustion engine. Then, heat of the exhaust gas G is transferred to the gas sensor 1 via the housing 41 attached to the mounting port 71 of the exhaust pipe 7. At the gas sensor 1, temperatures of the detection unit 21 of the sensor element 2 and the distal end side covers 45A and 45B disposed inside the exhaust pipe 7 become the highest. Further, at the gas sensor 1, the temperature becomes lower from the housing 41 toward a portion on the base end side L2 in the axial direction L. In other words, temperatures of the inner periphery side cover 5, the outer periphery side covers 46A and 46B, the sealing member 47, or the like, disposed outside the exhaust pipe 7 become low.

The sealing member 47, which is constituted with a rubber material, has lower heat resistance than a metal material, or the like, and thus, it is desired to maintain a temperature of the sealing member 47 low to prevent degradation. If an amount of heat transferred from the housing 41 to the outer periphery side covers 46A and 46B is greater, the sealing member 47 is heated via the outer periphery side covers 46A and 46B to a higher temperature.

At the gas sensor 1 of the present embodiment, particularly, according to a configuration where the inner periphery side cover 5 is in contact with the housing 41 and the distal end portions in the axial direction L of the outer periphery side covers 46A and 46B are in contact with the distal end portion in the axial direction L of the inner periphery side cover 5, and a configuration where the second thickness t2 of the inner periphery side cover 5 is greater than the first thickness t1 of the outer periphery side covers 46A and 46B, most heat from the housing 41 is transferred to the inner periphery side cover 5, so that an amount of heat which is transferred to the outer periphery side covers 46A and 46B can be reduced. Further, existence of the substantially cylindrical space 50 can minimize heat to be transferred from the inner periphery side cover 5 to the outer periphery side covers 46A and 46B.

This can suppress heat transfer from the housing 41 to the outer periphery side covers 46A and 46B from the outer periphery side covers 46A and 46B to the sealing member 47 disposed on the inner periphery side of the proximal end portions in the axial direction L of the outer periphery side covers 46A and 46B.

Thus, according to the gas sensor 1 of the present embodiment, transfer of heat from the housing 41 to the sealing member 47 can be suppressed, so that it is possible to effectively protect the sealing member 47 from heat.

<Confirmation Test>

In the present confirmation test, simulation was performed for the gas sensor 1 of the present embodiment which includes the inner periphery side cover 5 to confirm how much and to what degree of temperature respective portions of the gas sensor 1 are heated in a case where the exhaust gas G at 1100° C. flows inside the exhaust pipe 7 disposed at the gas sensor 1. Further, for comparison, simulation was performed in a similar manner also for a gas sensor in comparative example 1 in which the inner periphery side cover 5 is not provided and a gas sensor in comparative example 2 in which a heat dissipation member is provided on the outer periphery side of the outer periphery side covers 46A and 46B in place of the inner periphery side cover 5. In this simulation, distribution of temperatures of the respective portions of the respective gas sensors is displayed. Then, temperatures of the respective sealing members 47 at the gas sensor 1 of the embodiment and the gas sensors of comparative examples 1 and 2 were confirmed.

The temperature of the sealing member 47 at the gas sensor in comparative example 1 became approximately 260° C., and the temperature of the sealing member 47 at the gas sensor of comparative example 2 became approximately 250° C. Meanwhile, the temperature of the sealing member 47 at the gas sensor 1 of the embodiment became approximately 230° C. It was found from this result that, according to the gas sensor 1 of the embodiment using the inner periphery side cover 5, the temperature at which the sealing member 47 is heated can be made lower than the temperature at the gas sensors of comparative examples 1 and 2, so that it is possible to effectively protect the sealing member 47 from heat.

The inner periphery side cover 5 of the embodiment is constituted with stainless steel (SUS430) as a metal material. Meanwhile, the inner periphery side cover 5 can be also constituted with carbon steel (S45C) as a metal material to improve a heat transfer effect. While the thermal conductivity of stainless steel is approximately 16 [W/m·K], the thermal conductivity of carbon steel is approximately 50 [W/m·K].

It was found that in a case where the inner periphery side cover 5 is constituted with stainless steel, the temperature of the sealing member 47 can be lowered by approximately 30° C. compared to a case of the gas sensor in comparative example 1. Meanwhile, it was found that in a case where the inner periphery side cover 5 is constituted with carbon steel, the temperature of the sealing member 47 can be lowered by approximately 77° C. compared to a case of the gas sensor in comparative example 1. As a result of this, it was found that a metal material having higher the thermal conductivity is preferably used as the inner periphery side cover 5.

The present disclosure is not limited only to the embodiment, and it is possible to constitute further different embodiments within a scope not deviating from the gist. Further, the present disclosure incorporates various modified examples, modified examples within an equivalent range, or the like. In addition, various combinations of components, forms, and the like, assumed from the present disclosure are incorporated into technical idea of the present disclosure.

What is claimed is:

1. A gas sensor comprising:
    a sensor element which includes a detection unit which is capable of detecting a gas at a position on a distal end side in an axial direction thereof;
    a cylindrical housing in which the sensor element is disposed in a state where the detection unit projects on a distal end side in the axial direction;
    a contact terminal which is in contact with a terminal portion provided at a position on a base end side in the axial direction of the sensor element;
    an insulator holding the contact terminal;
    a lead wire connected to the contact terminal and drawn outside;
    a sealing member holding the lead wire;
    an inner periphery side cover mounted on an outer periphery of the housing at a position on the base end side in the axial direction; and
    an outer periphery side cover disposed on an outer periphery side of the inner periphery side cover, forming a substantially cylindrical space with the inner periphery side cover, and holding the sealing member on an inner periphery side, wherein
    a distal end portion in the axial direction of the inner periphery side cover is mounted on an outer periphery of the housing at a position on the base end side in the axial direction by bonding, press fitting or swaging,
    an end portion on the distal end side in the axial direction of the substantially cylindrical space is closed by an entire circumference of a distal end portion in the axial direction of the outer periphery side cover being mounted on an entire circumference of a distal end portion in the axial direction of the inner periphery side cover by bonding, press fitting or swaging,
    the substantially cylindrical space is formed by an outer diameter of the inner periphery side cover being smaller at the distal end portion in the axial direction than at a portion located on the base end side of the distal end portion, and
    an opening on the base end side in the axial direction of the substantially cylindrical space is open by a proximal portion in the axial direction of the inner periphery side cover being disposed on an inner periphery side of the outer periphery side cover,
    a bent portion which is bent on the inner periphery side with respect to a cylindrical body portion of the inner periphery side cover is formed at a proximal portion in the axial direction of the inner periphery side cover, a swage member being disposed between the bent portion and an end surface on the base end side in the axial direction of the insulator, and
    the insulator is accommodated in the cylindrical body portion of the inner periphery side cover.

2. The gas sensor according to claim 1, wherein the bent portion extends in a radial direction which is orthogonal to the axial direction of the sensor element.

3. The gas sensor according to claim 1, wherein
    the insulator is closer to the distal end side in the axial direction than the swage member; and
    the swage member is closer to the distal end side in the axial direction than the bent portion.

4. The gas sensor according to claim 1, wherein
    the bent portion directly contacts the swage member; and
    the swage member directly contacts the end surface on the base end side in the axial direction of the insulator.

* * * * *

UNITED STATES PATENT AND TRADEMARK OFFICE
CERTIFICATE OF CORRECTION

PATENT NO. : 12,222,312 B2
APPLICATION NO. : 17/526610
DATED : February 11, 2025
INVENTOR(S) : Shota Hagino Page 1 of 1

It is certified that error appears in the above-identified patent and that said Letters Patent is hereby corrected as shown below:

On the Title Page

The city of the third inventor Masato Ozawa incorrectly listed as "Nisshin" should be "Kariya.".

Signed and Sealed this
Eighteenth Day of March, 2025

Coke Morgan Stewart
*Acting Director of the United States Patent and Trademark Office*